United States Patent [19]

Jones

[11] Patent Number: 4,911,688
[45] Date of Patent: Mar. 27, 1990

[54] FLUID CONTAINING COVERS - WITH ELECTRICAL CIRCUITS

[75] Inventor: J. Paul Jones, Chester Springs, Pa.

[73] Assignee: Patent Research and Development Corp., Exton, Pa.

[21] Appl. No.: 219,437

[22] Filed: Jul. 15, 1986

[51] Int. Cl.⁴ .............................................. A61N 1/30
[52] U.S. Cl. ...................................... 604/20; 604/305
[58] Field of Search .................. 604/20, 24, 305, 289, 604/892.1

[56] References Cited

U.S. PATENT DOCUMENTS

| | | | |
|---|---|---|---|
| 3,367,332 | 2/1968 | Groves | 604/305 |
| 4,292,968 | 10/1981 | Ellis | 604/20 |
| 4,557,723 | 12/1985 | Sibalis | 604/20 |
| 4,564,016 | 1/1986 | Maurice et al. | 604/20 |
| 4,633,888 | 1/1987 | Yoneyama | 128/798 |

Primary Examiner—Lee S. Cohen
Assistant Examiner—Scott Getzow

[57] ABSTRACT

A clear cover to be placed on the skin of the human body to surround a wound on the skin (14), and to hold fluid (21) in contact with the wound. The cover has a flat, thin, flexible ring (1); the underside of which has an adhesive coating (7) to hold the ring on the body (14). A raised chamber (2) is formed by a thin flexible wall extending up from the ring (1), which has nipples (3) for being pierced by hypodermic needles (16); for filling the chamber (2) with fluid (21), and for venting air out of the chamber when the chamber is receiving fluid.

The above fluid containing cover having means to create free ions and an electrical field to enhance healing and regeneration of tissue; including a voltage source (10), a series resistance (11), and a metallic anode (12).

2 Claims, 5 Drawing Sheets

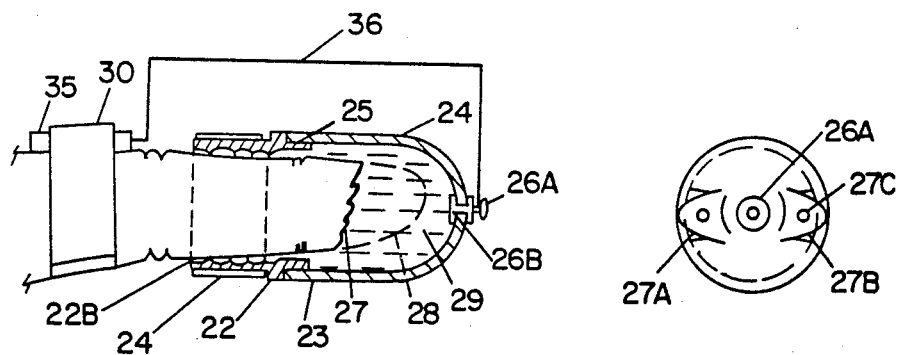
FIG. 5A
FIG. 5B
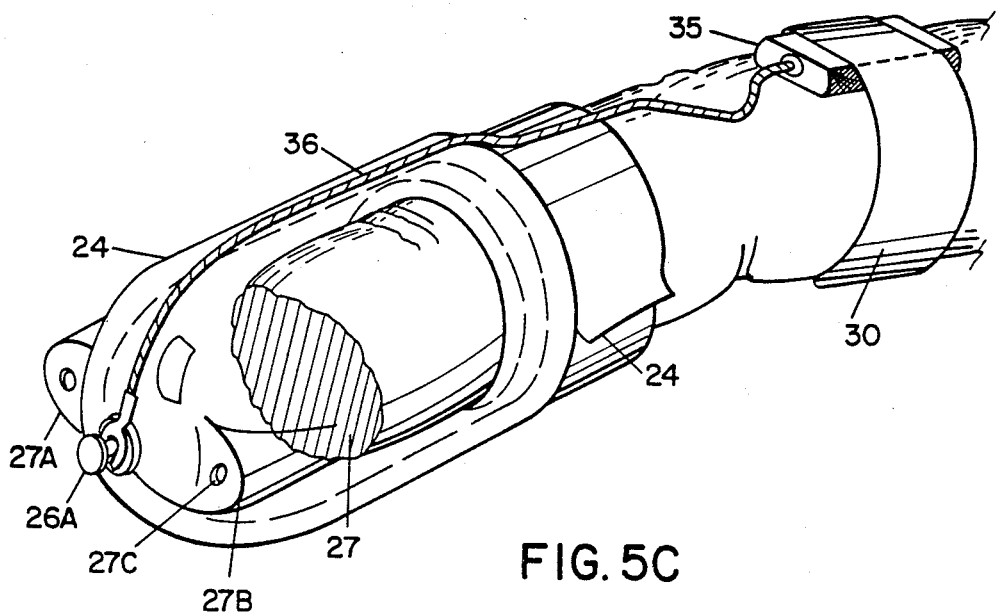
FIG. 5C

FLUID CONTAINING COVERS - WITH ELECTRICAL CIRCUITS

This invention relates to covers to be placed on the human body, and around a wound, to contain healing fluid in contact with the wound; and, in particular, to such covers which include electrical circuits for ion generation.

BACKGROUND

New research by medical institutions, and by major suppliers of protective covers for surface wounds, has been proving that all wounds heal quicker, and with much less scarring, if the are allowed to remain immersed in natural or synthesized body fluids. Various special waterproof tapes and pads are now available for covering superficial surface cuts, abrasions, etc.: to help retain body fluids that are exuded when a wound is still fresh, and to prevent drying out and/or scabbing.

The problems associated with ordinary bandages or adhesive tape covers are greatly amplified by any open wound in which a portion of the flesh has been evulsed; since a covering which is in contact with the open flesh of the wound can be partially captured in the new growth, or in an accompanying scab.

It is, therefore, one object of this invention to provide a flexible, self-adhering cover for surface wounds, which has a hollow chamber directly over the wound, to prevent material contact with the wound.

Another object of this invention is to provide a cover that is made of soft resilient material, such as clear silicone elastomer, which can be penetrated with hypodermic needles to fill with a healing fluid; and which can also be penetrated with hollow needles to flush out the fluid before refilling—such elastomer having the characteristic of "resealing" the puncture when the needle is removed.

Another object of this invention is to provide a clear covering which will allow the condition of a wound to be observed at any time, and especially after the sealed cover has been irrigated, or flushed out.

Still another object is to provide a cover of the kind, which has reinforcing ribs for providing additional crosswise strength, for holding a wound together without sutures; while still maintaining its flexibility in all planes of movement, other than crosswise to the length of the hollow chamber.

New developments in the study of cell growth, and particularly the work of Dr. Robert O. Becker, have shown the advantages of using very low concentrations of positive silver ions to combat bacterial infection; while not hindering normal cell growth or repair.

Therefore it is another object of this invention to provide a wound cover having therein a miniature circuit means for a voltage source, a series resistance, and a silver electrode.

There are substances, such as Dimethyl Sulfoxide (DMSO), which have the ability to penetrate the skin, and which can be used to carry other drugs or substances into the body.

It is, therefore, yet another object of this invention to provide a hollow body cover which may be employed as a delivery system for such substances.

In connection with the drawings noted below, the invention will be described with particular reference to covers for surface wounds; with means to generate positive silver ions for anti-bacterial action and to promote new cell growth.

FIG. 5A is an elevational view, partially in section, of a cover which is designed to protect and contain healing fluid for an amputated finger tip, with means to inject metallic ions into the fluid;

FIG. 5B shows the front end view of the cover of FIG. 5A; and

FIG. 5C is a pictorial view of the cover and ion injecting parts as shown in FIG. 5A.

Figure 1A:
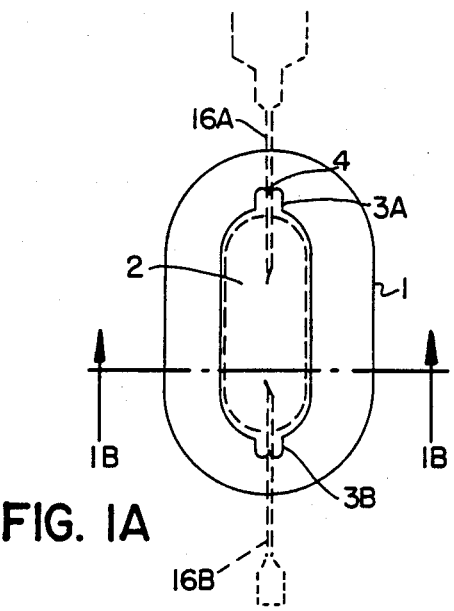
FIG. 1A is a plan view of a cover of the invention.

FIGS. 1A through FIG. 3 show the most typical configuration of a cover or "synthetic blister", which has a section in the form of a thin, flexible ring or flange 1, and another section in the form of an elevated, thin, flexible wall chamber 2. The desired flexibility is attained by molding the cover from soft silicone rubber, such as RTV 615 or equivalent, which is also transparent. The ring 1 is coated on the underside with an adhesive 7, such a Dow Corning 355, which will adhere to the skin. The adhesive surface is normally protected with a plastic strip (not shown) that is peeled off just prior to use. When the ring 1 is held on the skin, the chamber 2 is fluid tight, and is spaced from the wound 17.

The ring 1 and the chamber 2 are elongated and, in plan, the same are generally eliptical in shape. The opposite ends of the chamber 2 have thickened sections or nipples 3A and 3B, each having a small, elongated, slot-like recess 4 to guide the insertion of a hypodermic needle 16A with vial, and the insertion of another needle 16B, without vial, at the opposing end. The purpose of needle and vial 16A is to fill the chamber 2 with fluid, and the purpose of the needle 16B is to vent the air from the chamber 2 when fluid enters from the needle 16A.

Figure 2A:
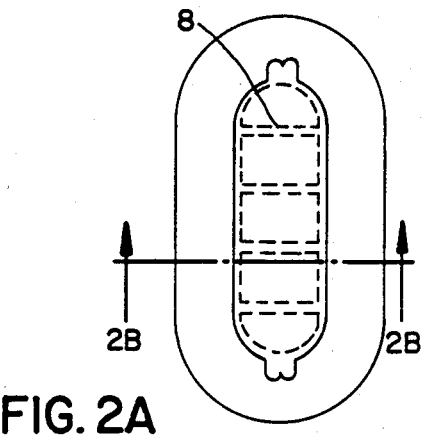
FIG. 2A is a plan view of another embodiment of the invention, incorporating reinforcing cross members.
Figure 1B:
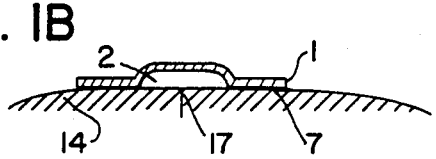
FIG. 1B is a cross sectional view of the cover taken along the lines 1B—1B of FIG. 1A, with the cover being mounted over the wound.
Figure 2B:
FIG. 2B is a view taken along the lines 2B—2B of FIG. 2A.
Figure 3:
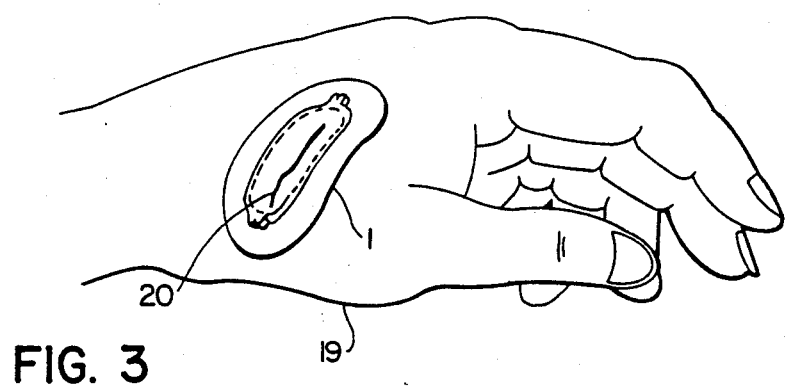
FIG. 3A shows a practical application of the cover; when located on an area of the body where the skin is constantly moving.

FIG. 2A shows the basic structure, with arch shaped ribs 8 added for cross sectional strength, while not affecting the stretching, bending or twisting flexibility of all other dimensions. With deep cuts or wounds 17 that may be near the point of requiring sutures, the extra strength of the ribs 8 can provide enough closure tension to eliminate the need for sutures, in many cases.

The flexible cover is designed to remain in place for up to one week, with changes of the healing fluids and with periodic irrigation with saline solution, if the situation requires it. The chamber 2, being formed from clear elastomer, makes the observation of the wound and the healing progress very easy. For clearing the chamber 2 of fluid, a hypodermic needle 16A is connected to a source of saline solution and the needle inserted in the nipple 3A; and another hypodermic needle 16B, connected to a drain tube, is inserted in the nipple 3B, and the chamber flushed. The chamber 2 is then refilled with healing fluid, as described above.

FIG. 3a shows a typical application of a blister cover, at a moving location over the thumb, that is usually difficult to bandage without loosing a good portion of the usage of the hand; (i.e. because of wrap around bandaging). The clear blister, which has skin-like properties, provides complete protection, a superior healing environment, and does not interfere with the hand 19 or thumb movement; even for a large cut as indicated at 20 (shown in full lines because of cover clarity.)

The invention is especially useful when wounds have missing (evulsed) flesh, which would tend to scar badly if a scab were allowed to form; or if a typical bandage were allowed to grow into the scab or wound, and had to be painfully removed. The use of the patients own blood or blood serum, as would be present in natural blisters, has been proven by workers in the field to be of great worth in reducing or eliminating scarring and accelerating the healing process.

In addition, the use of electric currents, of the order of 100 nano amps, has been found by researchers in the field to be very helpful in speeding up the regeneration of cells in wounds. When positive silver ions are added, most bacteria are killed without disturbing the growth of new cells; hence the addition of a circuit in the invention to accomplish the foregoing, as shown in FIGS. 4A through 4F.

Figure 4A:
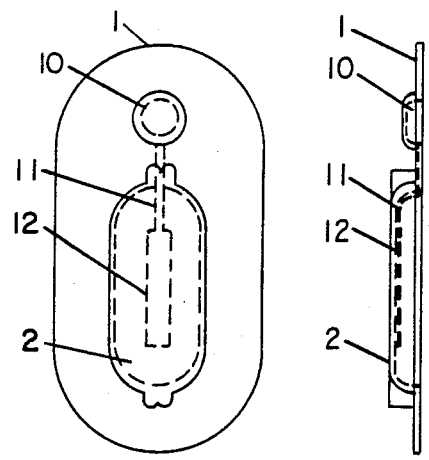
FIG. 4A is a plan view of the cover of FIG. 1A; including a circuit means.
Figure 4B:
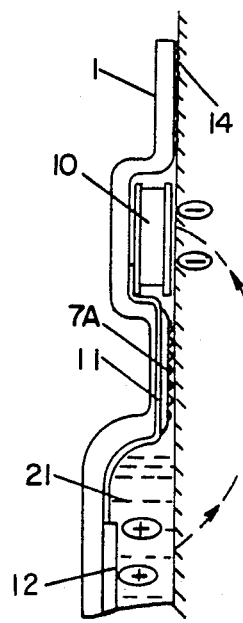
FIG. 4B is an enlarged, fragmentary view of elements of the cover of FIG. 4A, showing internal components.
Figure 4C:
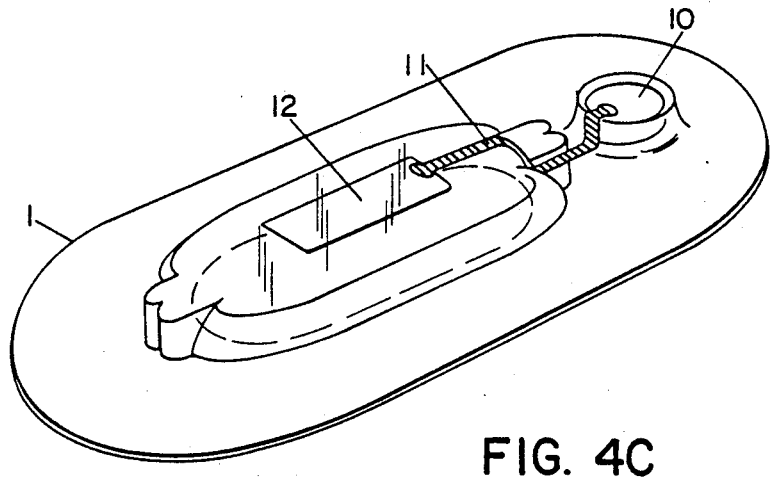
FIG. 4C is a pictorial view of the cover of FIG. 4A, showing the essential circuit parts.

The circuit elements include a battery 10, a series resistor 11, and a silver anode 12, shown in full line because of the transparent cover. The circuit elements are printed on the underside of the cover, and are protected by an overlaying seal (not shown). The negative battery terminal contacts the skin, and the positive battery terminal is connected to the silver plated anode 12 through the resistor 11. It will be understood that in printing the elements, such as the positive terminal of the battery 10, the terminal of the anode 12, and the connecting conductor, are all electrically insulated from the fluid 21 by a non-conducting overlay; with the negative terminal of the battery in contact with the skin, and the silver anode in contact with the fluid. The adhesive seal 7A separates the battery and the fluid. When the fluid is injected into the chamber 2, it constitutes an electrolyte conductor that completes a closed circuit through the body 14, as shown in FIG. 4B, and ion conduction automatically begins.

Figure 4D:
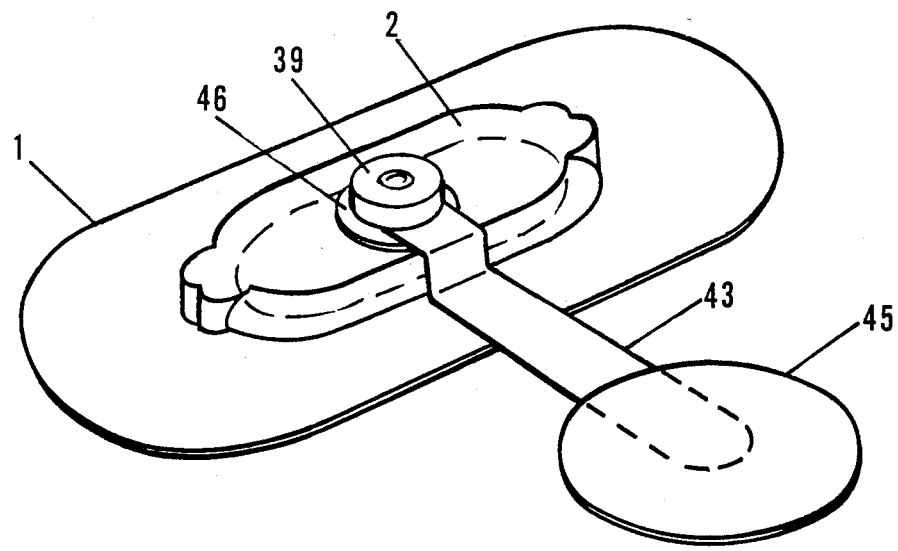
FIG. 4D is a pictorial view of the cover of FIG. 4A, with a thermoelectric version of the Silver anode and voltage source, which is a continuation of the invention in part, and which is made as a single unit that can be riveted on to the top of the elastomer chamber.
Figure 4E:
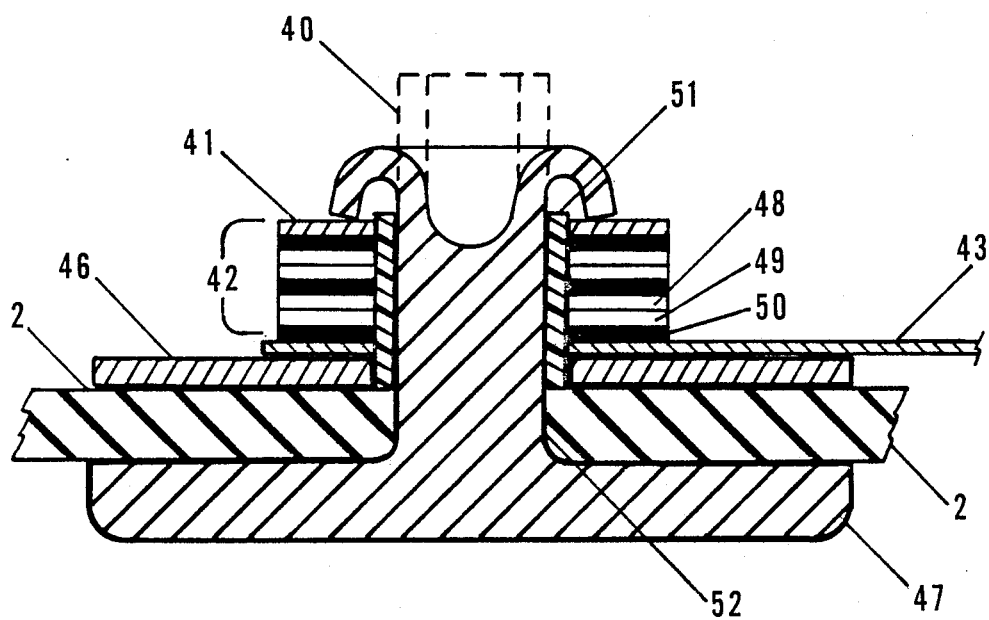
FIGS. 4E and 4F show cross sectional views of a multiple and a single junction thermoelectric assembly, which require only a single surface tab connection, as shown pictorially in FIG. 4D.
Figure 4F:
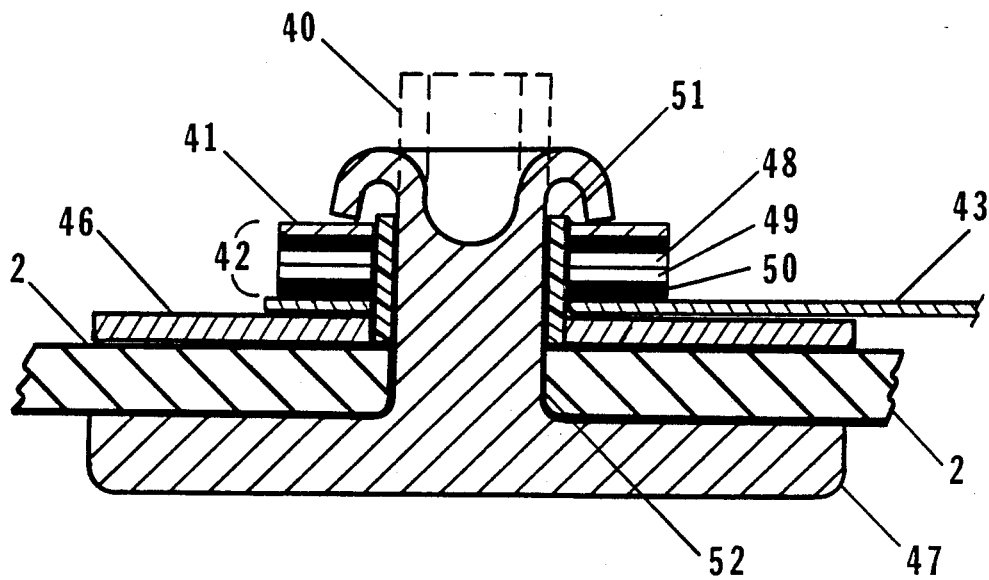

An alternate circuit installation method is shown in FIGS. 4D, 4E and 4F. A complete thermoelectric generator assembly 39, which is made up of pairs of dissimilar metal discs, is installed on a fluid containing cover 2, as shown in FIG. 4D. This single unit design is most useful in providing the positive ion source, as as add-on, for a wide variety of sizes and shapes of the basic Fluid Containing Covers.

The Thermoelectric Assembly 39 replaces the battery 10 and the series resistor 11 with a thermoelectric stack 42; which is designed to provide the very low voltages and associated low ion density (i.e. approximately 100 nano amps per square centimeter) with metallic discs 48, 49, typically copper and constantan, that generate thermoelectric current; with resistor discs 50, such as Cermalloy, to isolate the series junctions and establish the desired current limit.

The entire thermoelectric assembly is built upon an anode "rivet" with a broad head 47 and hollow ended stem 40, which is mounted through a hole 52 in the top of the fluid chamber 2, while in the unriveted state (see dotted lines). A compression washer 46 is first added; followed by the insulating sleeve 51. The rivet stem 40 is of the order of 0.080 inch in diammeter, and the metal discs 48 and 49, and the resistive conducting spacers 50, are approximately 0.250 inch in diameter.

The thermoelectric stack 42 is made up of one or more series connected pairs of Metal A 48 and Metal B 49 discs, which produce the desired voltage, plus interspersed resistive conductor discs 50, which set the ion current limit. In practice, these resistive spacers 50 could be deposited and fired on one surface of one type of metallic disc. The resistive discs have typical resistive values of 10K ohms to 100K ohms; with each pair of metallic discs 48, 49 providing approximately 0.001 volt, at body temperature. Since the thermoelectric stack 42 will normally always be near body temperature, the supplied ion current from the Thermoelectric effect will always be predictable and dependable; with no concern for the subminiature current source "running down", (i.e. since body heat generates the thermoelectric current).

Continuing the assembly steps: the ring shaped end of the negative skin electrode tab 43 is placed over the insulating sleeve 51; followed by a one or more sets of resistive conductor 50, metal A 48, and metal B 49, discs. The stack 42 ends with a non-metallic conductor 50, at the top of the stack. After the top washer 41, which is of like metal to the anode rivet, is added, the hollow end of the stem 40 is riveted, to complete the thermoelectric generator assembly 39.

The riveting operation forms a fluid seal between the compression washer 46, the Anode rivet head 47, and the compressible cover top 2; and also holds the stacked thermoelectric discs in permanent contact to each other. FIGS. 4E and 4F show multiple and single thermoelectric generator assemblies, with like numbers assigned to like parts.

At the time of riveting, the negative skin conductor tab 43 is led off at the desired angle, before it is compressed into the thermoelectric disc stack by the riveting operation.

WHEN APPLYING THE WHOLE COVER PRODUCT TO A PATIENT

1. The sterile seal (not shown) is peeled off the bottom adhesive surface of the cover ring pad 1; and the cover is applied to the skin, after suitable cleaning.

2. A dab of conductive paste is put on the bottom side of the negative skin electrode tab 43; which is then held in contact with the skin by an adhesive disc 45.

3. Healing fluid, which is electrically conductive, may then be injected into the chamber 2, by methods previously described.

4. The conducting fluid immediatley starts the desired ion flow by completing the circuit path from the Anode 40 to the body wound; and return through the skin electrode 43.

THE AMPUTATED FINGER VERSION

It has been known for many years that amputated finger tips will completely regenerate if treated properly (i.e. kept "bloody" and covered only—without sewing flaps of skin over the stump). Recently, the work of Illingsworth at Scheffield Childrens Hospital in England, and Dr. Michael Bleicher of New Yorks Mount Sinai Hosopital have been published; showing literally 100% results, in hundreds of cases, with children under eleven years of age. Success with adults has also been accomplished, using more elaborate means of supplying new blood to the regenerating area. The applicant has been involved in three successful adult cases, one of them being himself. The special version of fluid containing cover, which is designed to fit over an amputated finger tip stump, provides a practical and near ideal set of conditions for the missing finger tip to regenerate. The design is shown in FIGS. 5A through 5C.

This design has a section in the form of a flexible ring 22 and another section in the form of a flexible thin walled chamber 23. Both the ring 22 and chamber 23 are molded from clear silicone rubber, such as RTV 615 or equivalent. The chamber 23 is fused to the ring 22 at the interface 25 by a conventional silicone to silicone sealer. The chamber is adapted to receive fluid 29. The ring and chamber are made in a variety of sizes to fit the particular patient. Small fins 22B on the inside of ring 22 adjust for small differences in size and help seal the fluid 29 in the chamber 23. Medical tape 24 is used to apply a mild compression to the ring 22. At the front and center of the chamber 23 there is a metallic contact 25A, which is compressively mounted on the front wall of the chamber 23 to form the anode 26B. It is obvious from the prior discussion of the Thermocouple Anode Assembly, which is a continuation in part, that this alternate assembly could be substituted in place of the metallic contact 25A and some of the external circuitry components which will now be described.

FIGS. 5B and 5C show the nipples 27A and 27B set up on opposite sides of the amputated fingertip 28 of the finger 27, shown in full lines because of the transparent cover. The nipples have guide recesses 27C. The nipples and recesses serve the same function as the nipples 3A and 3B and recess 4 on the general fluid containing covers.

A metal case 35 containing a battery and a resistor is taped to the finger by the tape 30. The negative side of the internal battery is connected to the case with the positive side connected to the insulated conductor 36 which, in turn, is connected to the contact 26A.

When conductive fluid is in the chamber 23, a closed electrical circuit is established. This includes the negative battery terminal, the skin of the finger, the fluid in the chamber 23, the anode 26B, the conductor 36, and the positive side of the battery; which are all in series.

Besides providing a sterile environment for the amputated fingertip 27, and a cavity to contain the healing fluid 29, the invention provides an excellent bumper for mechanical protection of the open wound, which is the finger stump 27.

Although an oral antibiotic may be prescribed, no toxic substance is ordinarily introduced to the healing chamber, since the silver ions produced at the silver anode interface 26B provide an anti-bacterial function, and the low voltage field that is created between the anode 26B and the finger end 27, greatly enhances the regeneration process.

The nipples 3A, 3B, 27A, and 27B are formed of the same type of clear elastomer material as the chambers 2 and 23, and this is an advantage because, when an injected needle is pulled out, the puncture hole closes tight.

With respect to the material from which the cover is molded, I have specified silicone rubber RTV 615 because this material has the desired features. Further, I have specified silicone rubber in the claims for the same reason. It will be understood that the claims are intended to cover other materials which have the desired features, namely: inert, flexible, self-sealing, preferably transparent; and capable of being molded. The RTV 615 material is manufactured by the General Electric Co., Schenectady, N.Y.

I claim:

1. A cover to be placed on the human body over and around a surface wound thereon to hold healing fluid in contact with the wound, the cover being made of silicone rubber and having;

a thin, flexible ring having means to hold the ring on the skin of the body adjacent a wound thereon;

a hollow chamber formed by a thin, flexible wall connected to said ring and extending away from the ring so as to be spaced away from a wound when the ring is held on said skin;

first means on said wall to receive and permit a hypodermic needle to extend into the inside of said chamber by piercing the first means, the needle being for use in filling the chamber with fluid and the first means, when the needle is removed, closing off the pierced first means to prevent fluid from leaking therethrough.

second means on said wall to receive and permit a hypodermic needle to extend into the inside of said chamber by piercing the second means; the needle being for use in venting air out of the chamber when the chamber is receiving healing fluid from a hypodermic needle in said first means and the second means, when the needle is removed closing off the pierced second means to prevent fluid from leaking therethrough; and a thermoelectric stack made up of successive pairs of dissimilar metal discs interspersed with non metallic resistive discs to partially insulate each pair of metallic discs and establish the total series resistance of the stack, an anode rivet having a stem, an insulation cylinder surrounding the stem, the stack being assembled on said insulation cylinder surrounding the stem such stem penetrating said chamber, the thermoelectric stack including a first compressive washer on said chamber a negative skin electrode having a ring on the outside surface of said hollow chamber engaging said first washer, a second metal washer, the stack being connected to a top of said stem via a riveting operation to said second washer, which also provides compression to produce a seal for the stack to the chamber and good contact between all dissimilar metal discs, to establish an electrical circuit path which includes said negative skin electrode ring, the thermoelectric pairs of discs, the resistive discs, said anode rivet, the fluid in the chamber, and the body; with all in series to sustain a steady ion flow through the fluid and the wound that is in contact with the fluid in the chamber.

2. A cover to be placed on the human body over and around a surface wound thereon to hold healing fluid in contact with the wound, comprising:

a hollow chamber having securing means to secure the chamber to the body;

a first electrical current carrying member mounted on said chamber and having an inside portion inside the chamber and an outside portion outside of the chamber, the inside portion being constructed to be in contact with the fluid in the chamber; a second current carrying member mounted on said chamber to be in contact with the body when the cover is mounted on the body;

the material of the chamber, said securing means, and said first electrical current carrying member constructed to retain healing fluid within the chamber when the cover is mounted on the body; and thermoelectric means including first and second elements made of dissimilar metal in electrical contact with one another, a first thick film resistor in electrical contact with said first element, and in electrical contact with said outside portion, a second thick film resistor in electrical contact with said second element and with said second current carrying member whereby to establish an electric circuit through said fluid and said body.

* * * * *